(12) United States Patent
Brenner

(10) Patent No.: US 11,020,069 B2
(45) Date of Patent: Jun. 1, 2021

(54) DENTAL X-RAY SENSOR HOLDER AND DENTAL X-RAY SENSOR SHEATH THEREFOR

(71) Applicant: DENTSPLY SIRONA Inc., York, PA (US)

(72) Inventor: Tod Brenner, Pequea, PA (US)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 16/002,270

(22) Filed: Jun. 7, 2018

(65) Prior Publication Data

US 2019/0029617 A1    Jan. 31, 2019

Related U.S. Application Data

(63) Continuation-in-part of application No. 15/658,760, filed on Jul. 25, 2017.

(51) Int. Cl.
| | | |
|---|---|---|
| *A61B 6/14* | (2006.01) |
| *A61B 6/00* | (2006.01) |
| *G03B 42/04* | (2021.01) |
| *G03B 42/06* | (2021.01) |

(52) U.S. Cl.
CPC ............ *A61B 6/145* (2013.01); *A61B 6/4423* (2013.01); *A61B 6/587* (2013.01); *G03B 42/042* (2013.01); *G03B 42/06* (2013.01)

(58) Field of Classification Search
CPC ...... A61B 6/145; A61B 6/4423; G03B 42/042
See application file for complete search history.

(56) References Cited

U.S. PATENT DOCUMENTS

| | | | |
|---|---|---|---|
| 2006/0193442 A1* | 8/2006 | Quarry ................... | A61B 6/145 378/170 |
| 2011/0164733 A1* | 7/2011 | Steward, Jr. ........... | G03B 42/04 378/170 |

* cited by examiner

*Primary Examiner* — Hugh Maupin
(74) *Attorney, Agent, or Firm* — Dentsply Sirona Inc.

(57) ABSTRACT

A dental x-ray sensor holder and sheath for affixing a sensor to a backing plate of the holder. The dental x-ray sensor holder and sheath generally includes a sensor holder with a backing plate, having one or more spring arms, and affixed to or formed contiguously with a proximal end of a bite block of the holder. It also includes a sensor sheath adapted to secure a sensor to the backing plate for X-ray acquisition.

11 Claims, 27 Drawing Sheets

DENTAL X-RAY SENSOR HOLDER AND DENTAL X-RAY SENSOR SHEATH THEREFOR

CROSS REFERENCE TO RELATED APPLICATIONS

This is a Continuation-In-Part of U.S. patent application Ser. No. 15/658,760 filed on Jul. 25, 2017, which is a patent application claiming the benefit of and priority to U.S. Provisional Patent Application Ser. No. 62/366,741, filed on Jul. 26, 2016 and Provisional Patent Application Ser. No. 62/401,956, filed on Sep. 30, 2016 which are herein incorporated by reference for all purposes.

BACKGROUND OF THE INVENTION

Field of the Invention

The present disclosure relates generally to a holder and a sheath and more specifically to a dental X-ray sensor holder and a corresponding dental X-ray sensor sheath for removably securing a sensor in said sheath to a backing plate of said holder for X-ray acquisition.

Related Art

A conventional dental X-ray acquisition can be performed by positioning an X-ray source on one side of a patient and transmitting X-rays through a site in the oral cavity to be irradiated, and toward an x-ray detector located in the oral cavity.

U.S. Pat. No. 3,473,026 discloses a device for positioning dental X-ray film within the mouth for producing radiographs. It is hereby incorporated by reference for background purposes.

In a manner similar to the use of x-ray films, holding and positioning devices have been developed for x-ray sensors and phosphor imaging plates.

One way Dental X-rays sensors have been positioned for image acquisition is through the use of adhesives. More specifically adhesives are used to bond a holder to an encapsulated film or sensor as disclosed in U.S. Pat. No. 6,811,312.

U.S. Pat. No. 7,004,627 discloses a barrier and cushioning apparatus for use with sensors as a means to avoid contamination of the sensor while providing reduced discomfort through the use of a cushion cover that may incorporate an integrated adhesive section for securing to a positioning accessory such as a sensor holder.

However these holders can be bulky and accompanying adhesives may be time consuming to apply to holders when multiple radiographs are needed. Moreover, some adhesives may not be suitable to be used in the oral cavity. It is therefore desired to create a holder that is compact, inexpensive, simple and eliminates the use of adhesives to hold X-ray detectors.

Multiple types of X-ray detectors exist. A dental X-ray film for example is positioned relative to the target site in a predetermined and secure manner in order to obtain a useful image.

More recently, traditional X-ray films have been replaced with X-ray sensors. An example of such a sensor is shown in U.S. Pat. No. 6,652,141 which is hereby incorporated by reference for background disclosure of X-ray sensors.

Phosphor imaging plates are also used in the dental industry. The imaging plate is irradiated and the x-ray shot is stored onto the imaging plate to be read later by a scanning machine or the like and the data is transferred to a storage or display device, such as a computer.

These and other type of devices that receive dental X-rays for dental purposes are hereinafter collectively referred to as dental X-ray imaging media, X-ray sensors, sensors, imagers, image media or the like. Any such devices that are sensitive to such X-rays is within the scope of the disclosure. It is envisioned that in the future, other type of dental imaging media will be developed using similar or perhaps completely different technologies. These all have at least some commonality in that they generally must fit within the oral cavity and they must be securely held in a desired location during the x-ray procedure.

It will be appreciated from the above discussion that the different image media holders while all accomplishing similar purposes, all operate in different manners. However, the need still exists to create a device that is compact, inexpensive, simple and eliminates the use of adhesives to hold X-ray detectors.

BRIEF SUMMARY OF THE INVENTION

Existing limitations associated with the foregoing, as well as other limitations can be overcome by a method and system for removably securing a sensor to a backing plate of a dental X-ray sensor holder using a sheath provided with a strap wherein the strap can receive the backing plate of the holder to physically impinge on it and thereby secure the sensor in position relative to the backing plate. The disclosure thus comprises a sensor holder with a backing plate, having one or more spring arms and affixed to or formed contiguously with a proximal end of a bite block of the holder, and a sensor sheath adapted to removably secure a sensor in said sheath to the backing plate of said holder for X-ray acquisition.

There has thus been outlined, rather broadly, some of the features of the disclosure in order that the detailed description thereof may be better understood, and in order that the present contribution to the art may be better appreciated. There are additional features of the disclosure that will be described hereinafter.

In this respect, before explaining at least one embodiment of the disclosure in detail, it is to be understood that the disclosure is not limited in its application to the details of construction or to the arrangements of the components set forth in the following description or illustrated in the drawings. The disclosure is capable of other embodiments and of being practiced and carried out in various ways. Also, it is to be understood that the phraseology and terminology employed herein are for the purpose of the description and should not be regarded as limiting.

An object is to provide a Dental X-ray sensor Holder and Sheath for operably affixing a sensor to a backing plate of said holder. The sheath also acts as a contamination barrier for the sensor.

Another object is to provide a Dental X-ray Sensor Holder and Sheath that eliminates the use of conventional adhesives to affix a sensor to a backing plate of a sensor holder.

Another object is to provide a Dental X-ray Sensor Holder and Sheath wherein the sheath is provided with a strap that is permanently affixed to the sheath to provide a means for attaching the sensor in the sheath to a backing plate of the sensor holder.

Another object is to provide a Dental X-ray Sensor Holder and Sheath wherein the backing plate of the holder, provided with spring arms, which when slid under the strap of the sheath causes the strap to pull on the sheath to tighten it around the sensor.

Another object is to provide a Dental X-ray Sensor Holder and Sheath that for use with different sizes of sensors by having a backing plate with spring arms wherein the arms can extend outwardly to tighten the sheath around the different sized sensors.

Another object is to provide a Dental X-ray Sensor Holder and Sheath wherein the holder is configured for anterior teeth X-ray acquisitions.

Another object is to provide a Dental X-ray Sensor Holder and Sheath wherein the holder is configured for posterior teeth X-ray acquisitions.

Another object is to provide a Dental X-ray Sensor Holder and Sheath wherein the holder is configured for bitewing horizontal X-ray acquisitions.

Another object is to provide a Dental X-ray Sensor Holder and Sheath wherein the holder is configured for bitewing vertical X-ray acquisitions.

Another object is to provide a Dental X-ray Sensor Holder and Sheath wherein the holder is configured for bitewing endodontic X-ray acquisitions.

Further features and advantages, as well as the structure and operation of various embodiments herein, are described in detail below with reference to the accompanying drawings.

To the accomplishment of the above and related objects, this disclosure may be embodied in the form illustrated in the accompanying drawings, attention being called to the fact, that the drawings are illustrative only, and that changes may be made in the specific construction illustrated and described within the scope of this application.

BRIEF DESCRIPTION OF THE DRAWINGS

The teachings claimed and/or described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION OF THE INVENTION

Figure 1:
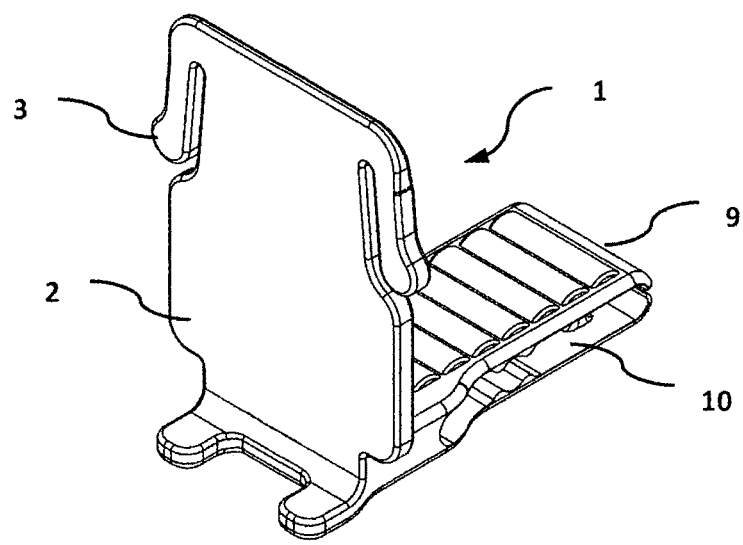
FIG. 1 is a perspective view of the preferred embodiment of the present disclosure, used for X-ray acquisitions of the anterior teeth.
Figure 2:
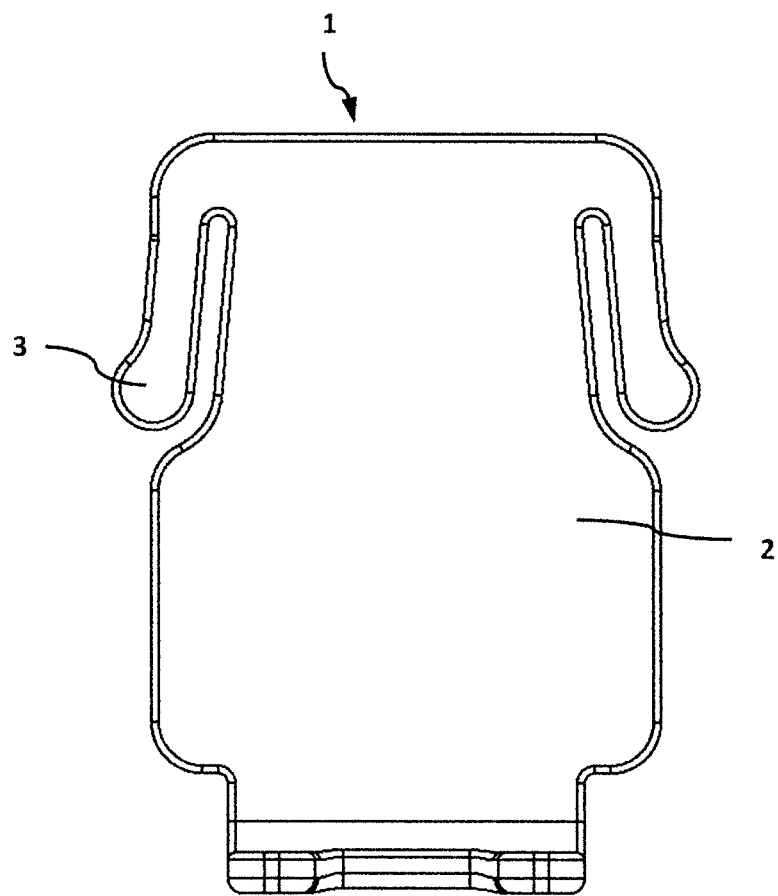
FIG. 2 illustrates a rear view of the sensor holder of FIG. 1.
Figure 3:
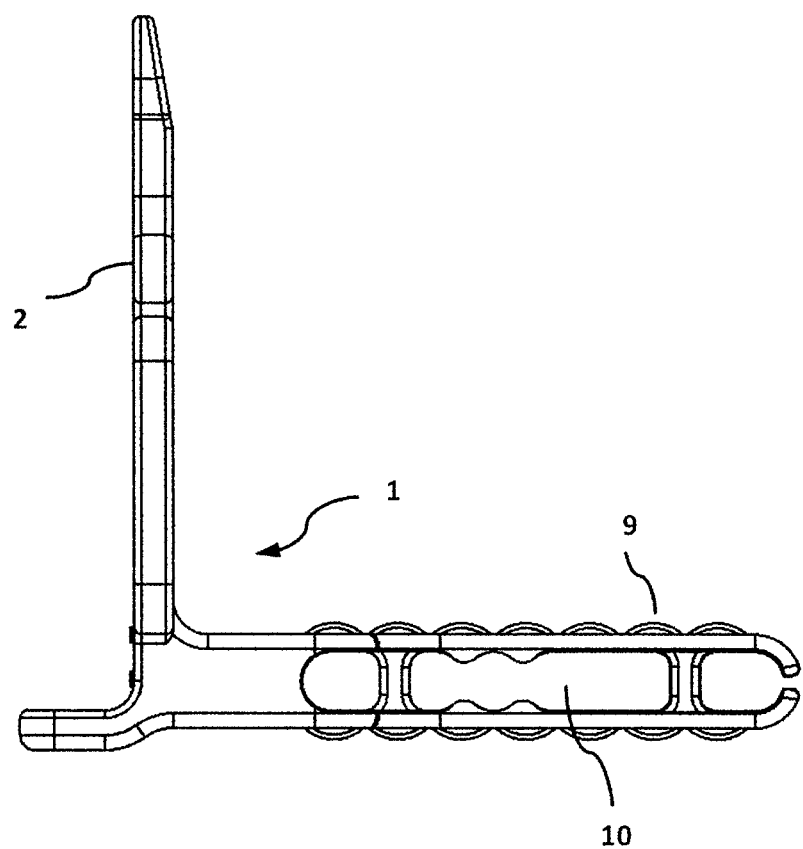
FIG. 3 is a side view of the sensor holder of FIG. 1.
Figure 4:
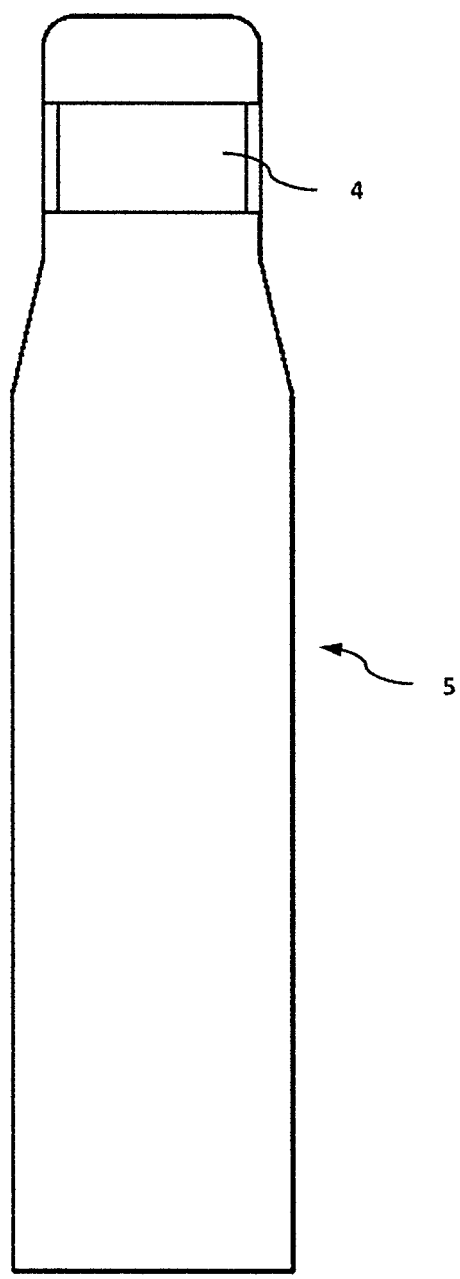
FIG. 4 illustrates a top view of a sensor sheath with a strap firmly sealed to the edges of the sheath.
Figure 5:
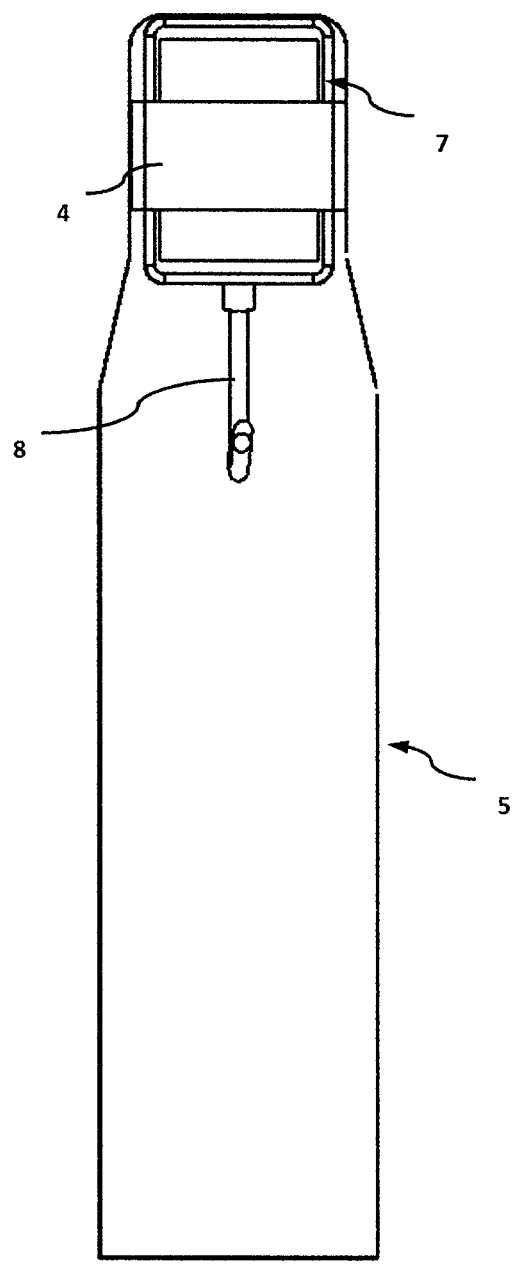
FIG. 5 shows a top view of a sensor sheath according to the present disclosure with a sensor inserted inside.
Figure 6:
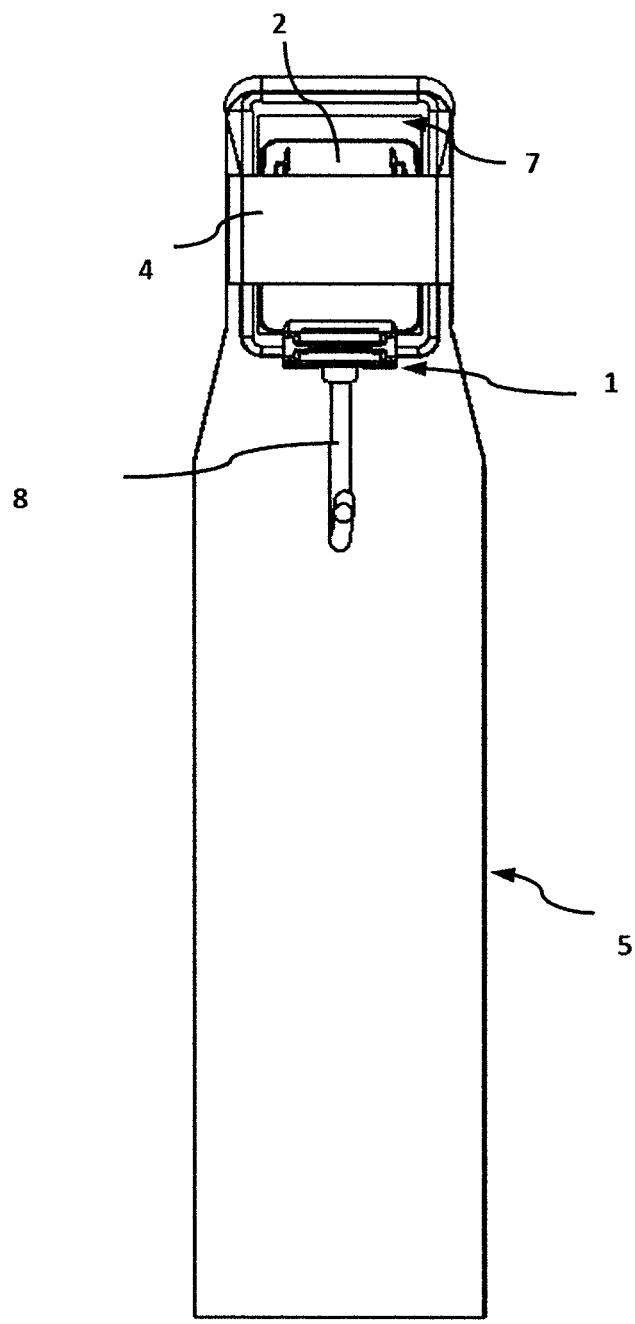
FIG. 6 shows a top view of the sensor/sensor sheath combination of FIG. 5 in use with the strap of the sheath being affixed to the sensor holder of the present disclosure.

In accordance with example aspects described herein, a sensor holder and sheath are provided for X-ray image acquisition. Focusing now descriptively on the drawings, in which similar reference characters denote similar elements throughout the several views, the figures illustrate a sensor holder with a backing plate, having one or more spring arms and affixed to or formed contiguously with a proximal end of a bite block of the holder, and a sensor sheath adapted to removably secure a sensor to the backing plate for X-ray acquisition.

Holder 1

Figure 8:
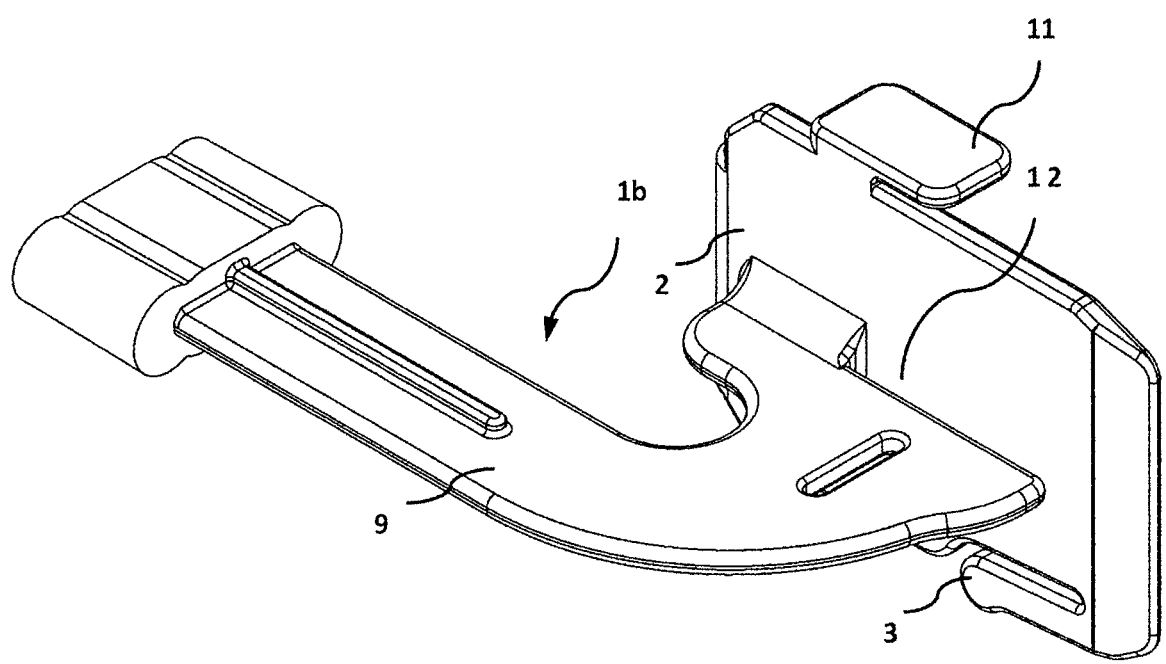
FIG. 8 shows a perspective view of an alternate embodiment of the holder, showing a holder for bitewing horizontal X-ray acquisitions.
Figure 10:
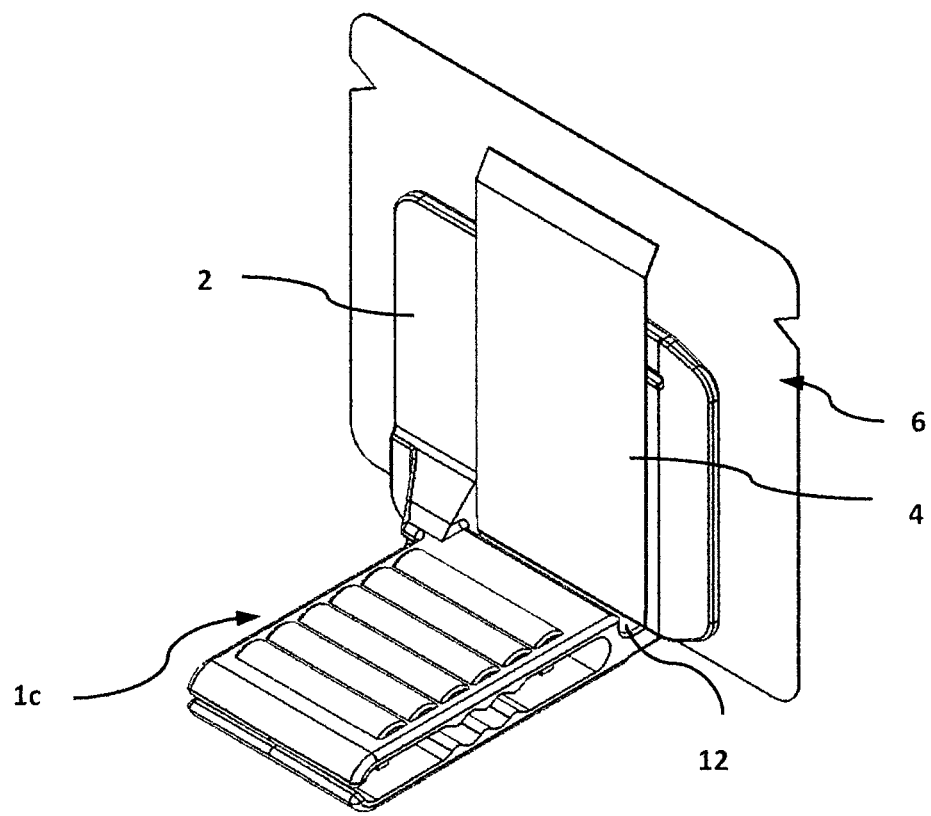
FIG. 10 is an upper perspective view of the holder of FIG. 1, connected to an alternate embodiment of the sensor sheath of the present disclosure, which alternate embodiment is a phosphor plate barrier with a strap sealed to it for engaging with the backing plate of the sensor holder.

Turning now to the sensor holder of FIG. 1, a backing plate 2 extends from the proximal end of a bite block 9. The backing plate 2 has a plurality of spring arms 3 which project outwardly from the backing plate 2. The backing plate is made of a fairly stiff material to ensure that an affixed sensor 7 is in parallel alignment with an aiming ring (not shown) for X-ray acquisition. The spring arms are adapted to slide easily under the strap 4 of a sensor sheath 5 and pull on the sheath 5 to tighten it which in turn keeps the sensor 7 in place. Alternative embodiments herein may also have sensor alignment tabs 11 to prevent the rotation of the sensor 7 when in use. This is especially helpful for posterior periapical and bitewing horizontal X-ray acquisitions wherein the sensor is attached to the backing plate in its horizontal position, (FIGS. 8 and 10).

The bite block 9 of the holder has slots 10 in which an aiming arm (not shown) is inserted preferably through a friction fit manner for further connection to an aiming ring (not shown). The bite block and holder in general may be of myriad shapes and sizes appropriate to allow for disparate positioning in the mouth of a patient during image acquisition procedures. As is known in the art, the bite block 9 of the X-ray sensor holder will be positioned in a patient's oral cavity (not shown) and the patient will be instructed to bite upon the block. This locates the secured X-ray sensor during the ensuing dental imaging acquisition procedure. Alternative embodiments of the holder may have a channel 12 (FIG. 8) in which a strap 4 of a sheath 5 fits. Another alternative embodiment may have an arrow 13 on a side of the backing plate to indicate the direction of insertion of the holder 1 under the strap 4.

Sheath 5

The sensor sheath 5 is adapted for connection to the backing plate 2 of a holder by the use of a strap 4 sealed to the sheath. The strap 4 can be affixed onto one side of the sheath by conventional methods used in the industry such as by heat staking or welding it along the short edges only. Alternatively, the strap 4 can be a loop around the sensor sheath 5 and preferably, it is made of a thick film strip capable of withstanding the force exerted by the spring arms 3 of the holder 1.

The X-ray sensor 7 slides easily into the sheath when the sheath is not engaged to the holder. When the holder 1 is then slid in under the strap 4 of the sheath 5, the spring arms 3 pull up on the strap 4 which in turn pulls up on the sheath 5 and tightens it around the sensor 7 to keep it 7 in place. Different shapes and sizes of the sheath and strap, such as the phosphor plate barrier envelope/sheath 6 (shown in FIG. 10), can be realized for varied sensors and dental X-ray acquisition positions. The cable 8 of the X-ray sensor allows for transmission of the sensor data to a receiver in a conventional manner.

In accordance with this disclosure, the sheath 5 may be an X-ray sensor sheath that is adapted with a simple, flexible and mildly elastic plastic band that is firmly attached on the edges to a preferably clear film of sheath through such conventional methods as welding or heat staking. The strap 4 is attached at a position on the sheath such that the it pulls on the sheath 5 to tighten it around the sensor when the backing plate of a holder is inserted to fit tightly underneath it.

Alternative Embodiments of Disclosure

The holder is preferably molded from a single piece of thermoplastic such as polyethylene to ensure that X-rays pass evenly and unhindered therethrough.

Figure 7:
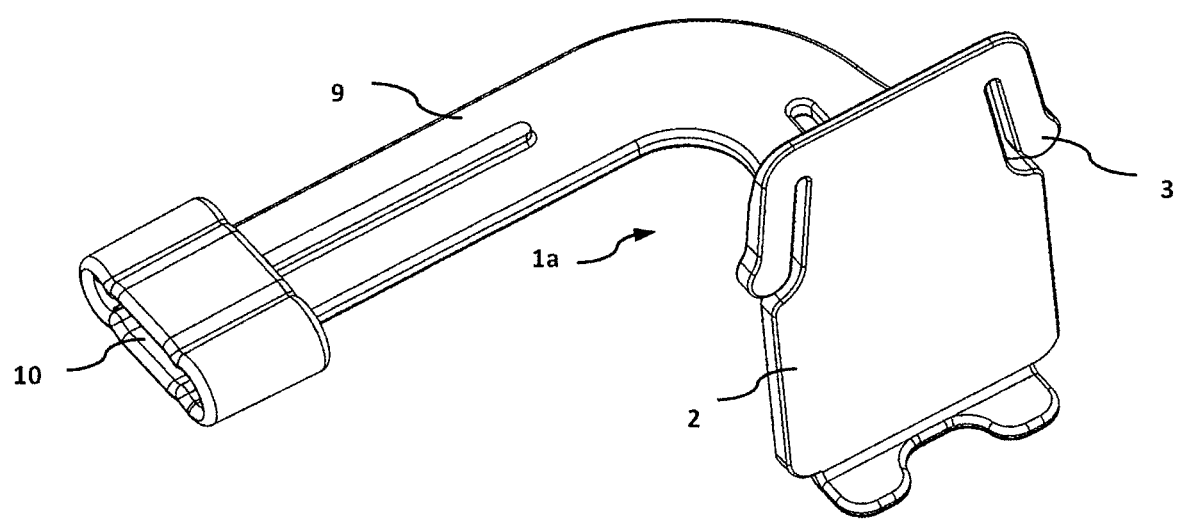
FIG. 7 illustrates a perspective view of an alternate embodiment of the holder, showing a holder for bitewing vertical X-ray acquisitions.
Figure 9:
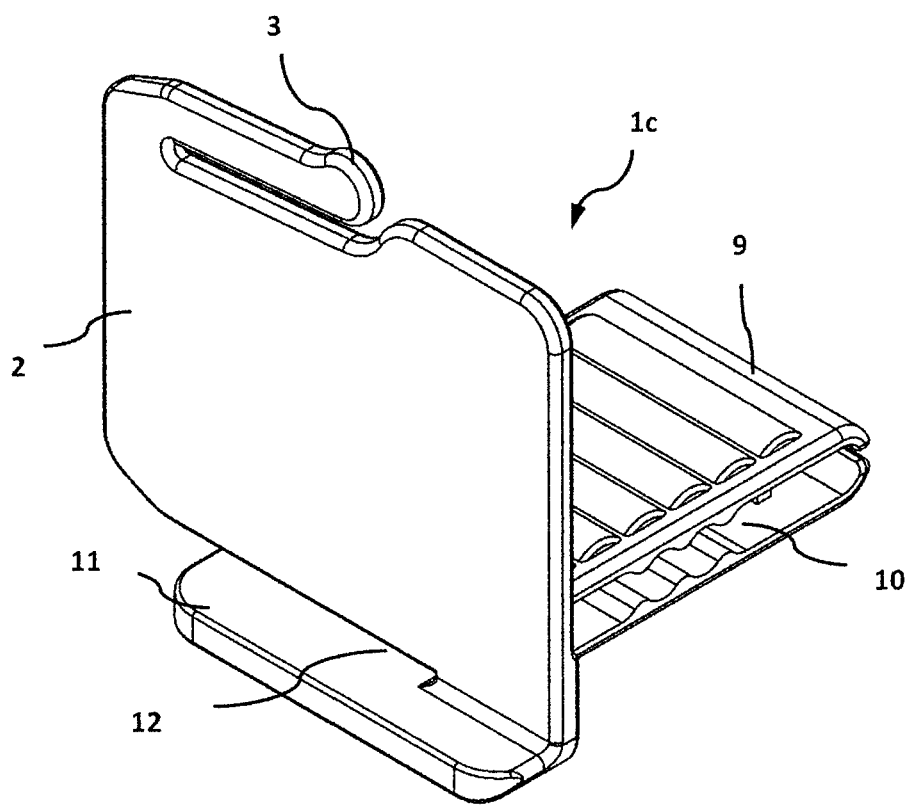
FIG. 9 illustrates a perspective view of an alternate embodiment, showing a posterior holder for X-ray acquisitions of the posterior teeth.
Figure 11:
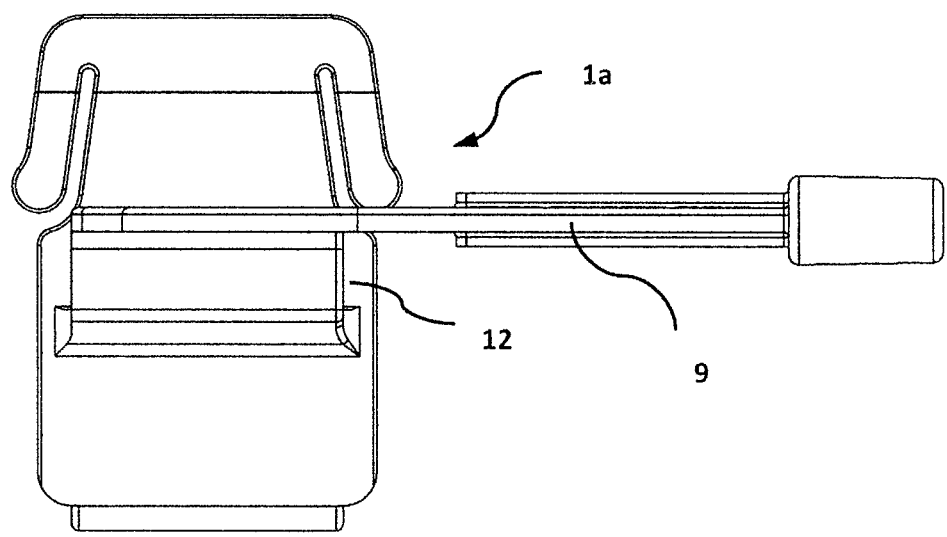
FIG. 11 shows a rear view of the holder of FIG. 7.
Figure 12:
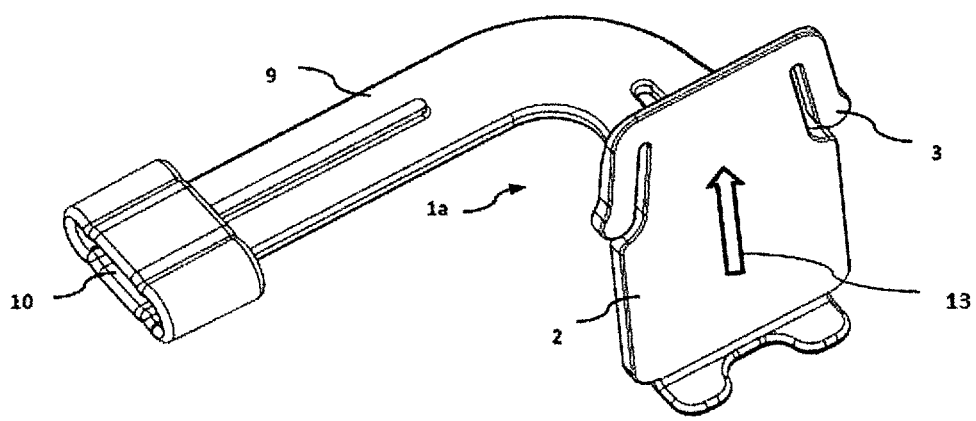
FIG. 12 shows an alternative embodiment of the holder with an arrow on a side of the backing plate.

FIGS. 7-9 show alternative embodiments of the sensor holder. FIG. 10 shows an alternative embodiment of the sheath in use Turning now to FIG. 7, an illustration of a bitewing vertical holder 1a is shown. A backing plate 2 having spring arms 3 projecting outwardly from said backing plate 2 extends contiguously from the proximal end of an elongate bite block 9. The bite block 9 is joined to the backing plate 2 at a mid-region so it rests along the occlusal arch of the teeth to be radiographed. Located at a first end of the bite block 9 are slots for a conventional aiming arm (not shown) for connection to an aiming ring (not shown). Located at a second end of the bite block 9 is a channel 12 (shown in FIG. 11) for receiving the strap 4 of a sheath 5 of the present disclosure. The backing plate 2 can also be constructed to have a ledge (not shown) with a depression for receiving an envelope 28 with a phosphor plate inserted in it.

FIG. 8 illustrates a bitewing horizontal holder 1b with a backing plate 2 and an elongate bite block 9. In addition, a sensor alignment tab 11 may extend from the backing plate to correctly position an attached sensor during X-ray acquisitions to minimize distortion and improper focus resulting from incorrect alignment. A channel 12 is provided for receiving the strap 4 of a sensor sheath 5 of the present disclosure.

FIG. 9 shows a posterior holder 1c for imaging teeth in the posterior region of an oral cavity comprising a backing plate 2, spring arm 3 and bite block 9. Like other embodiments, the holder is provided with a channel 12 for receiving the strap 4 of a sheath 5 of the present disclosure. A sensor alignment tab 11 allows for arranging a sensor in an appropriate position for imaging.

FIG. 10 shows an alternative embodiment of a sheath in use. A strap is preferably permanently attached to a phosphor plate barrier/sheath 6 using conventional means. The strap is likewise preferably a simple, flexible and mildly elastic plastic band that is firmly welded or heat staked to the phosphor plate barrier. In another alternative embodiment of the phosphor plate barrier, as shown in FIGS. 13-16, the barrier has a front film 15 and a back film 14 wherein the front film 15 is welded or attached in similar fashion along the sides and bottom edges to the back film 14 and between which a phosphor plate (not shown) is inserted. The top edge 16 of the front film 15 is not welded to the back film 14 providing an entrance for insertion of the phosphor plate. The back film 14 is has a strap 4 welded to it along the short edges of the strap 4. When the phosphor plate is inserted, the back film 14 is bended 17 and sealed to the front film 15 after a protective liner 18 on the front film 15 is removed to expose an adhesive coating (not shown). This makes the strap 4 of the barrier tight and ready for insertion of a holder 1.

Figure 17:
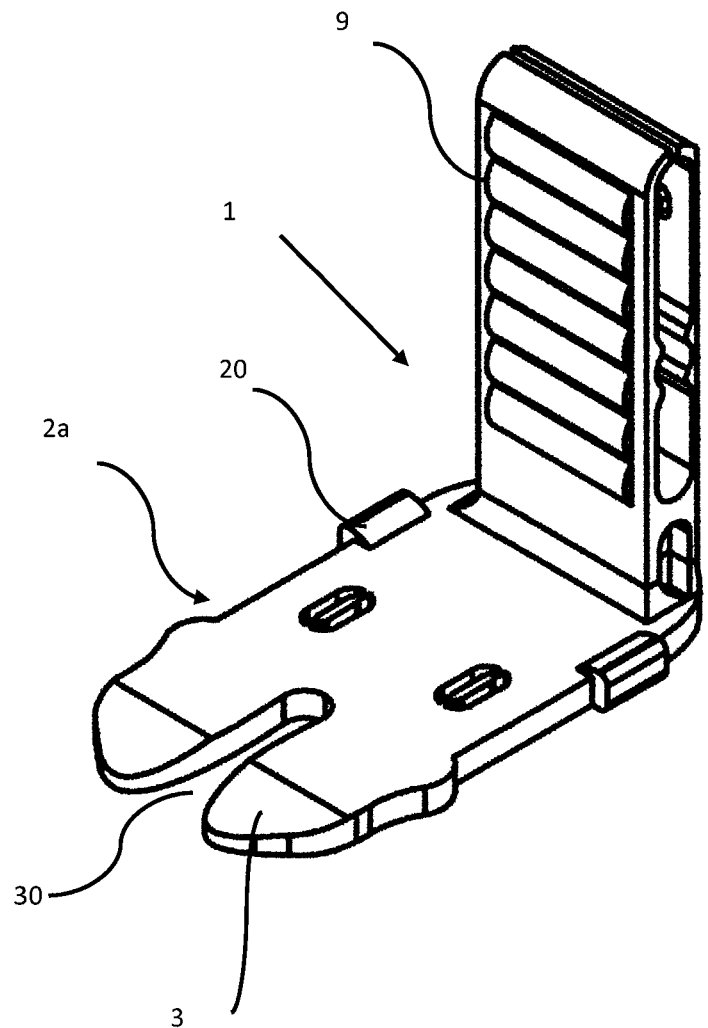
FIG. 17 illustrates a perspective view of an alternate embodiment of the holder, showing a size 0 anterior holder.
Figure 18:
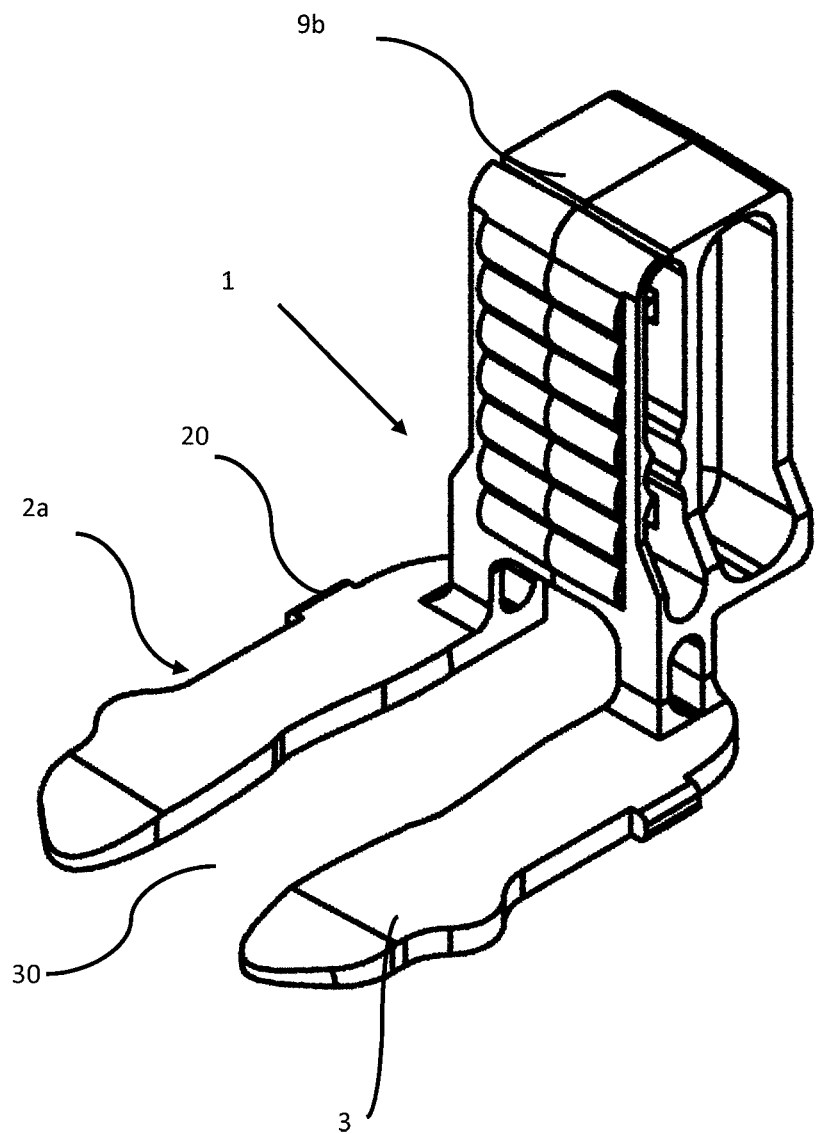
FIG. 18 illustrates a perspective view of an anterior thick biteblock holder.
Figure 19:
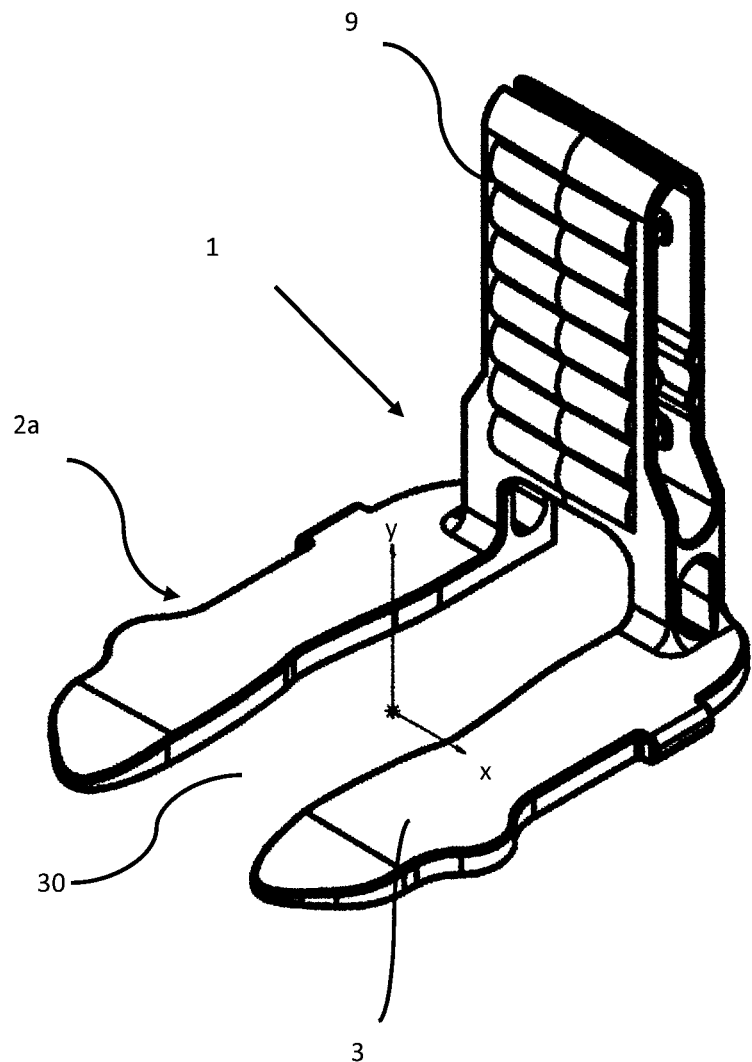
FIG. 19 shows a perspective view of an alternate embodiment of the holder which is an anterior thin biteblock holder.
Figure 22:
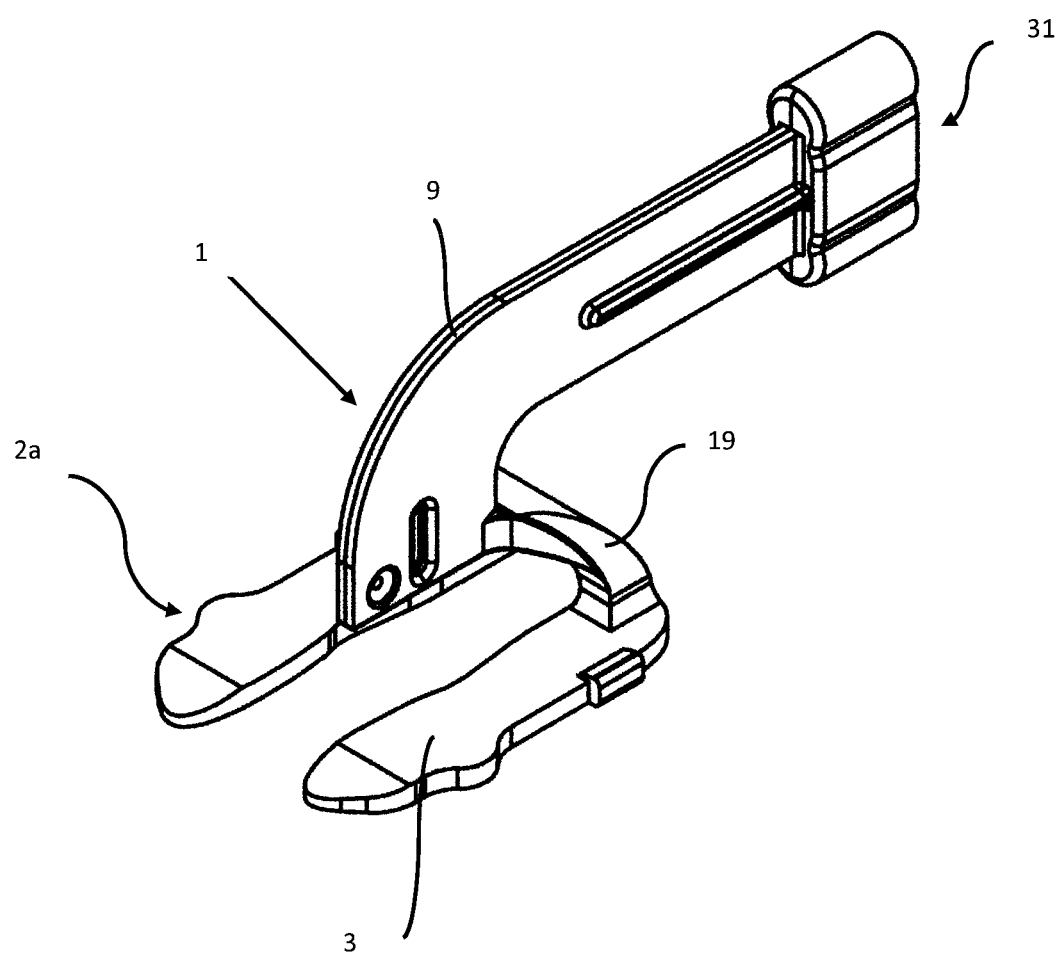
FIG. 22 is a perspective view of a bitewing horizontal holder.
Figure 23:
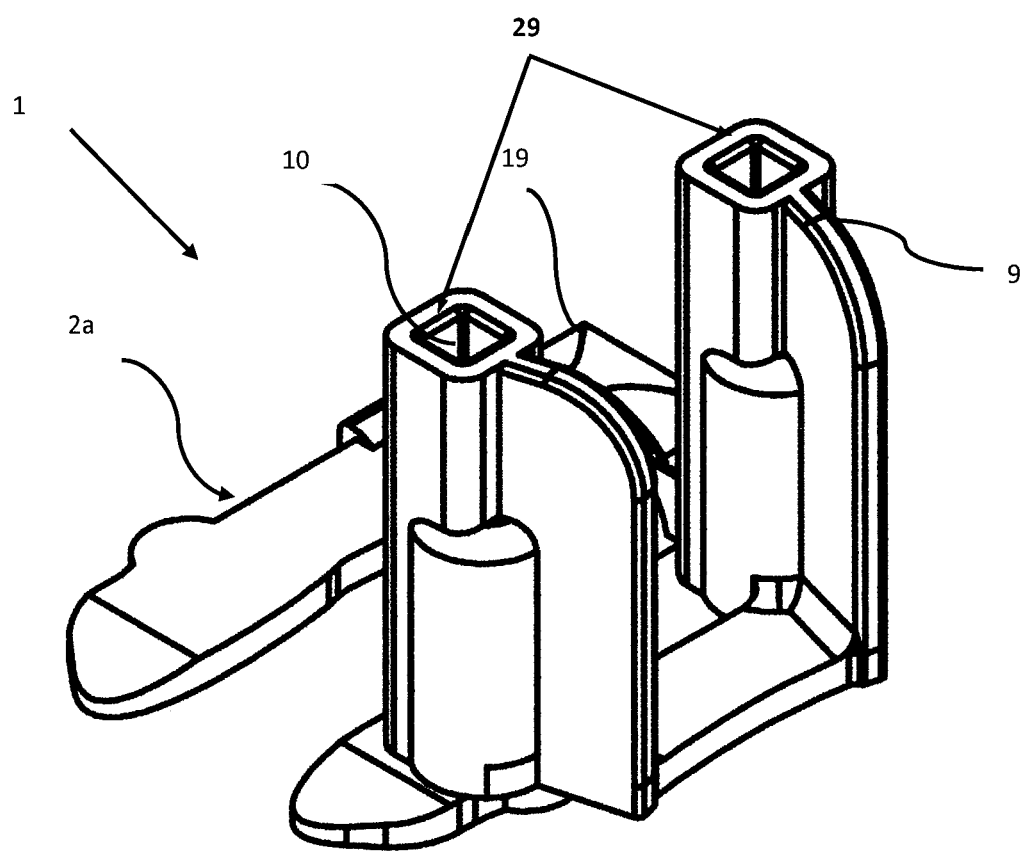
FIG. 23 illustrates a perspective view of an endodontic horizontal holder.
Figure 24:
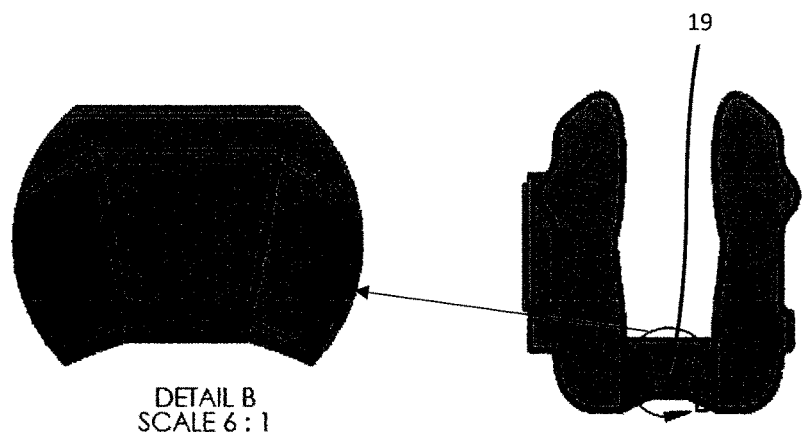
FIG. 24 shows an enlarged view of a taper feature of the holder.

FIGS. 17-28 show further embodiments of the holder 1 wherein the holder 1 may hold different sized sensors such as size 0, 1 or 2 sensors. Turning descriptively to FIGS. 17 and 19, an embodiment of the backing plate 2a, wherein the backing plate 2a itself comprises two spring arms 3, may lie in a horizontal plane passing through the axis x of the holder 1, as shown in FIG. 19. The spring arms 3 of the backing plate 2a may be separated by a clearance 30 that extends along a fraction of the length of the backing plate 2a as shown in FIG. 17 or fully along the entire length of the backing plate as shown in FIG. 18. As shown in FIG. 18, the backing plate may sometimes consist essentially of two spring arms 3 wherein said two spring arms 3 may be right angles to the bite block 9. The two spring arms 3 in all embodiments may enable squeezing to generate a large degree of compression and thus allow holding different sized sensors. The backing plate 2a may be connected to the biteblock 9 by a connecting mass 19. The connecting mass 19 may comprise bevel surfaces as shown in FIG. 24 which may give the holder 1 a taper feature that allows the spring arms to move or substantially move in said horizontal plane without deflecting down. This may allow the spring arms 3 to bend freely when compressed without losing their horizontal profile relative to the vertical bite block. This is advantageous because deflection may otherwise arch the backing plate 2a, affecting the position of a digital sensor or phosphor plate and causing a corresponding reduction in image quality during an imaging procedure. In some embodiments, the bite block 9 may be directly connected the backing plate as shown in FIG. 17. The two spring arms 3 may also be connected to each other by the connecting mass 19 as shown in the posterior biteblock holder 1 of FIG. 26. The backing plate 2*a* may comprise tabs 20 that hold a strap 4 in place and/or serve as positioning means for location in an imaging procedure. The holders may be used with phosphor plates or digital sensors.

Figure 13:
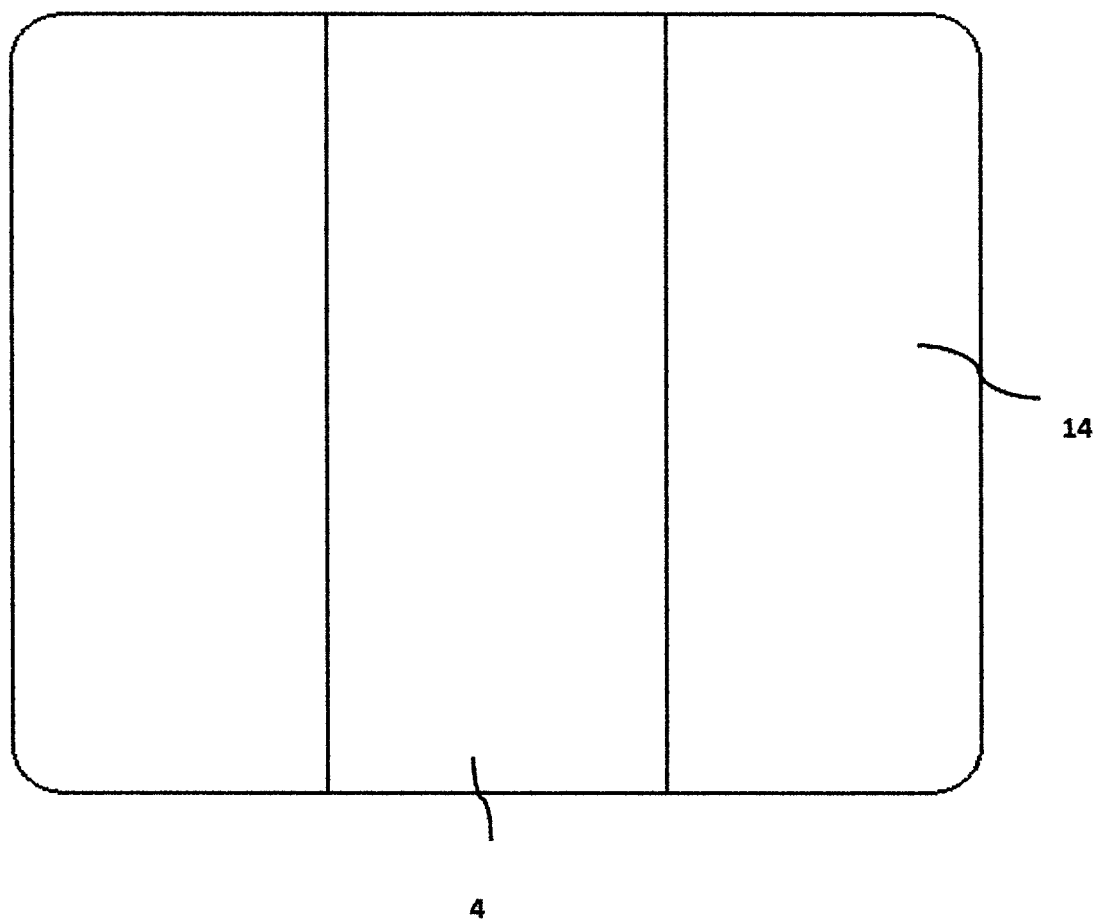
FIG. 13 illustrates the back film and strap of another embodiment of the phosphor plate barrier of the disclosure
Figure 14:
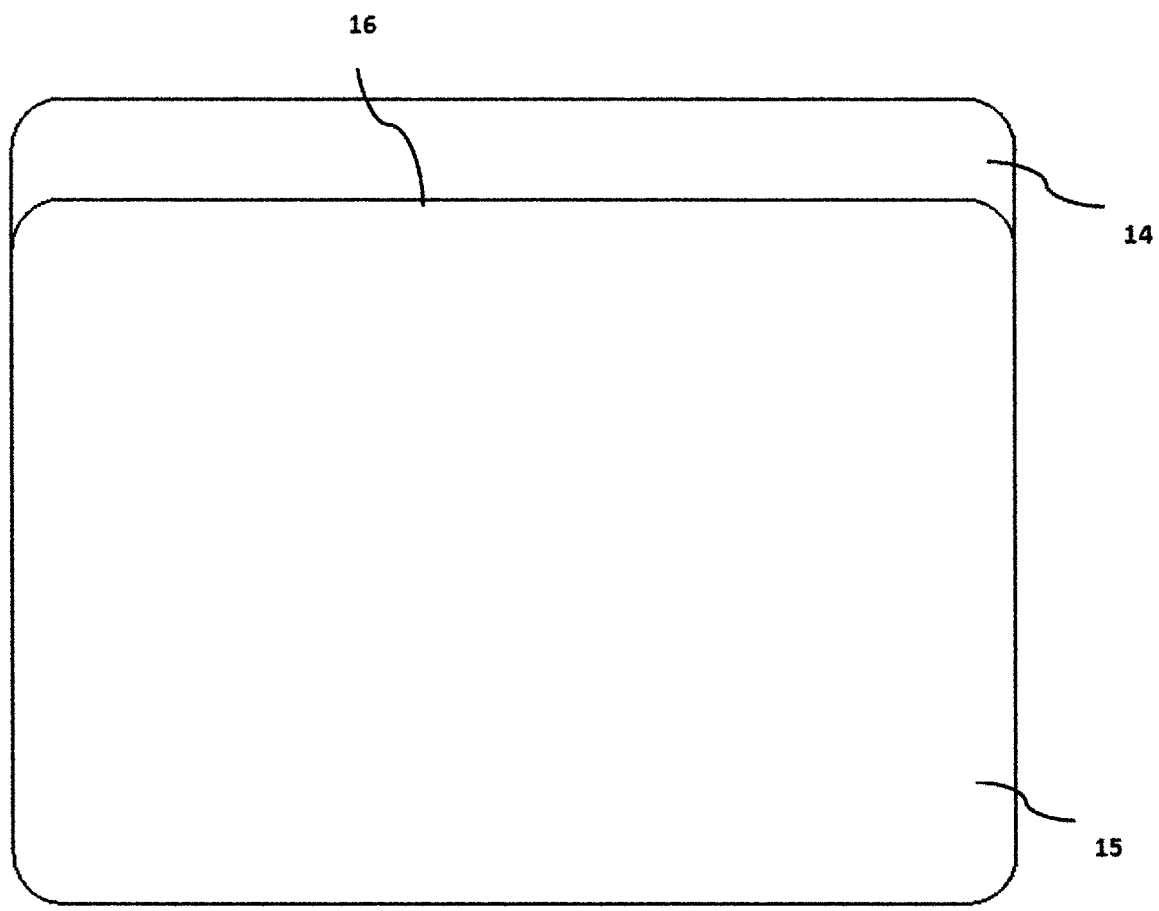
FIG. 14 illustrates the back film of FIG. 13 welded to the front film.
Figure 15:
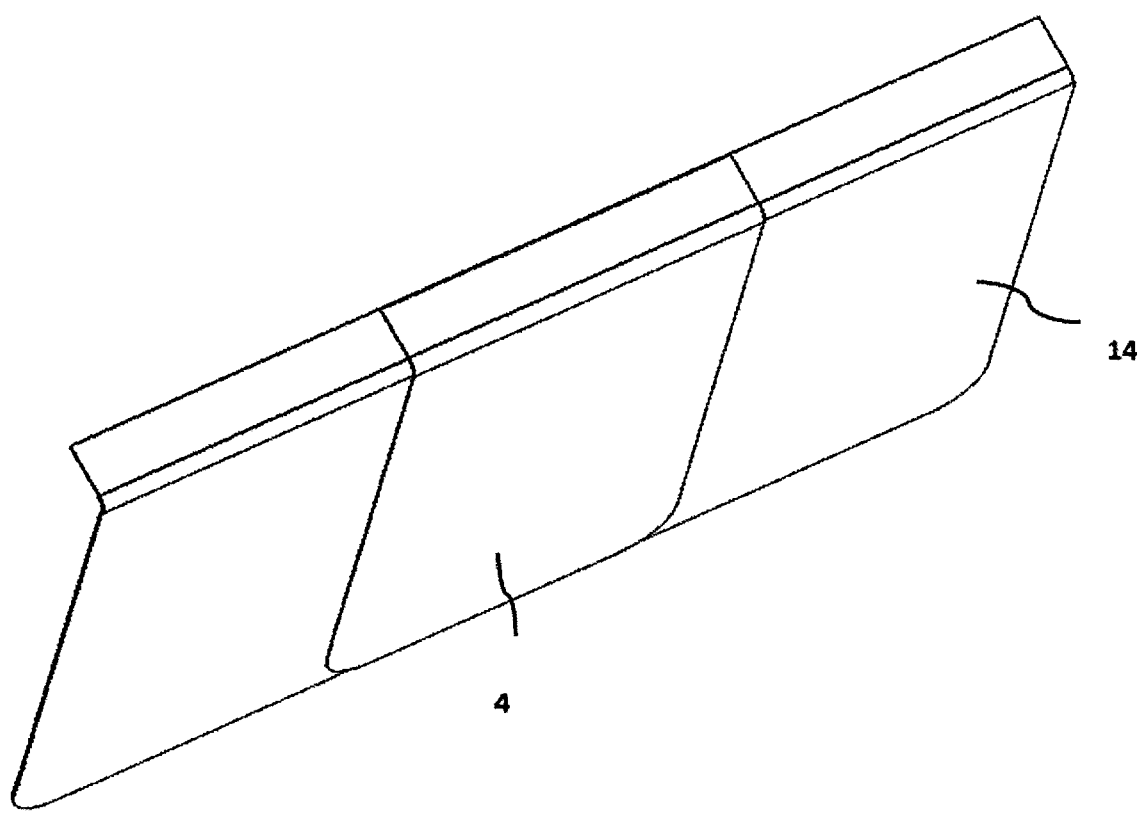
FIG. 15 shows an upper perspective view of the back film and strap of FIG. 13 with the upper part of the back film bended.
Figure 16:
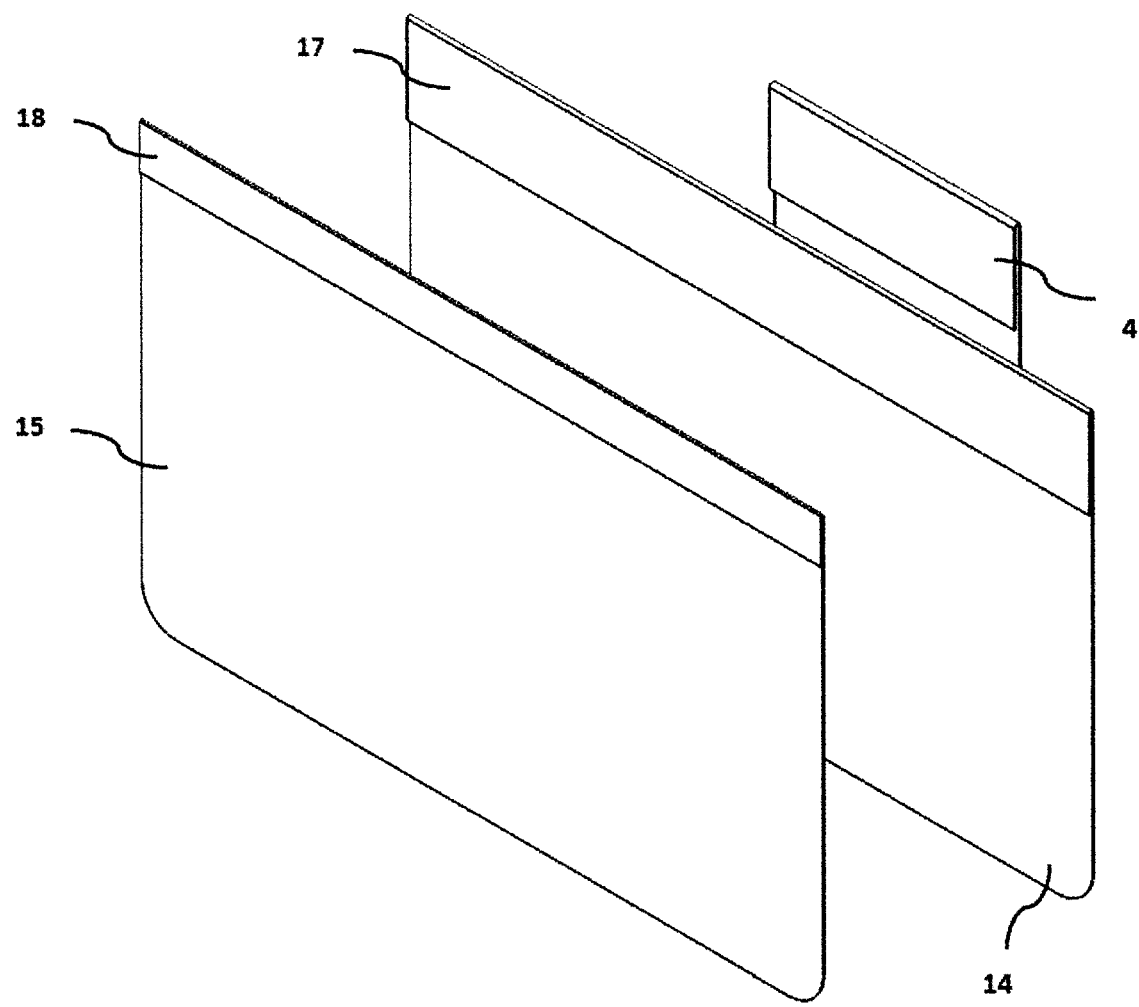
FIG. 16 is an exploded view of the phosphor plate barrier embodiment of FIG. 13 showing the back film, front film and strap.
Figure 25:
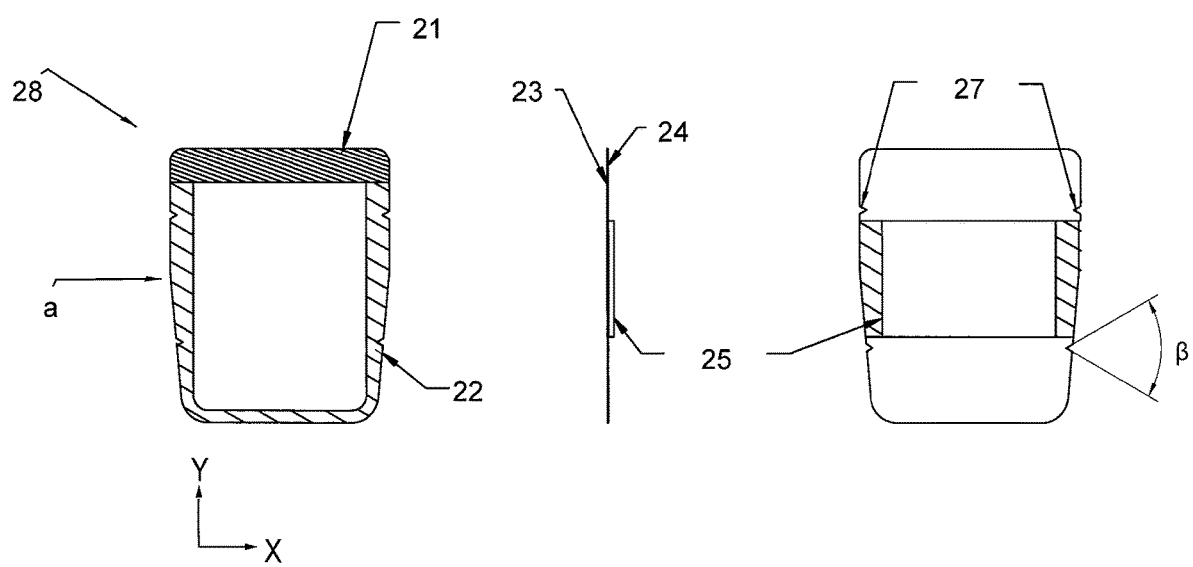
FIG. 25 shows an envelope of the present disclosure.
Figure 26:
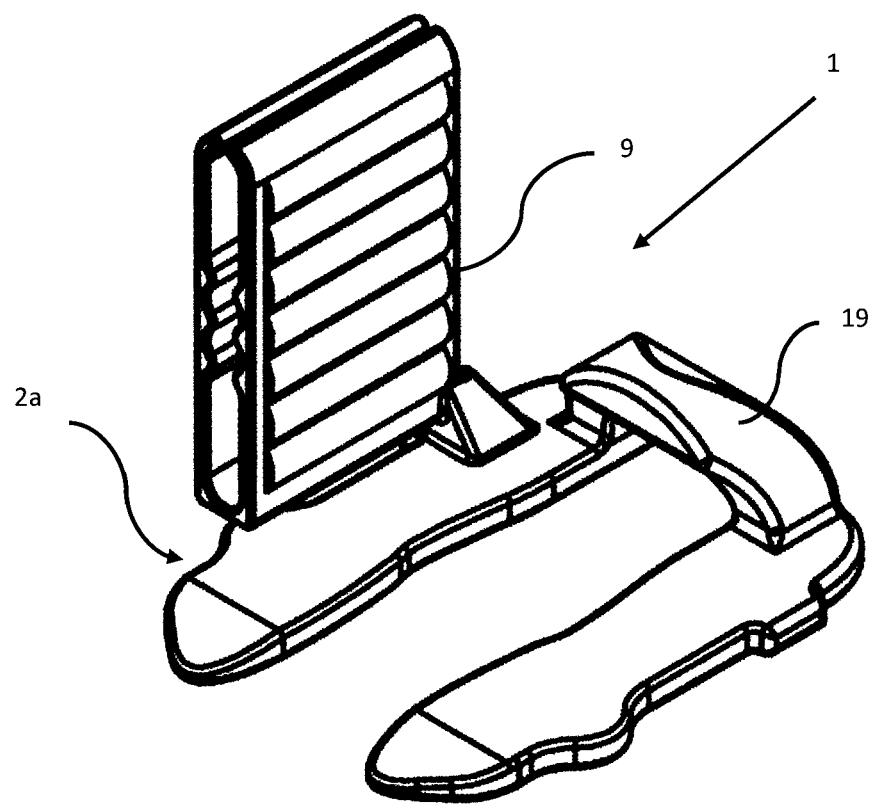
FIG. 26 illustrates a perspective view of a posterior biteblock holder.

In an embodiment of the envelope of FIG. 13, FIG. 25 shows an envelope 28 that may receive sensor such as a phosphor plate for imaging. The envelope may comprise an adhesive 21 applied to a preferably clear film 24. A back side film 23 of the envelope 28 which may preferably be black may receive no adhesive. The envelope 28 may further comprise a heat seal area 22 as shown in FIG. 25. The envelope 28 may be constructed with a plurality of notches 27, and preferably 2 or 4 notches (1 or 2 pairs of notches) close to the strap 25 such that after an imaging procedure, the envelope 28 may be torn open along a longitudinal direction X to expose the inserted phosphor plate such that a phosphor plate scanning system such as VistaScan can grasp the plate without a user having to manually push or walk said plate out of the envelope 28. In an embodiment herein, the notches 27 may have a "V" shape such that tearing of the envelope can be achieved along a horizontal line X or substantially horizontal line. In an further embodiment herein the "V" shaped notches may have an angle of 45°-75°, (for example, 60°). The heat seal area 22 may be constructed to bulge out at a location a to enable gripping of the envelope 28 when tearing without also pulling on an inserted phosphor plate. In a further embodiment, the envelope 28 may be made of soft material such as a polyurethane elastomer (Dureflex PT-9400S). In yet another embodiment the envelope may have rounded edges to reduce gagging of patients. The envelope 28 may be constructed with different sizes such that different sizes of sensors can be used for example, size 0, 1, 2 or 3 sensors.

Figure 28:
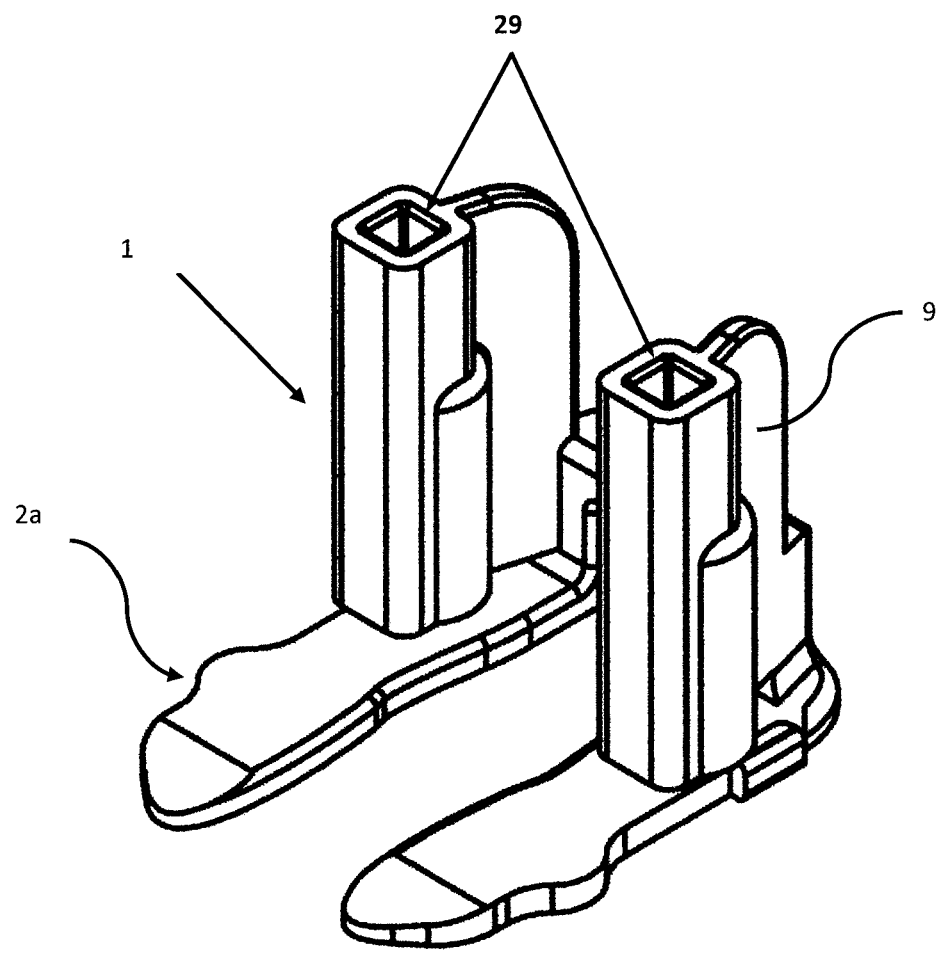
FIG. 28 illustrates a perspective view of an endodontic vertical holder.

In further embodiments of the holder as shown in FIG. 23 and FIG. 28, the holder may be an endodontic horizontal holder or and endodontic vertical holder respectively wherein the holder is provided with clearance structures 29, wherein said clearance structures provide clearance for movement of an endodontic file (not shown) during treatment.

Figure 20:
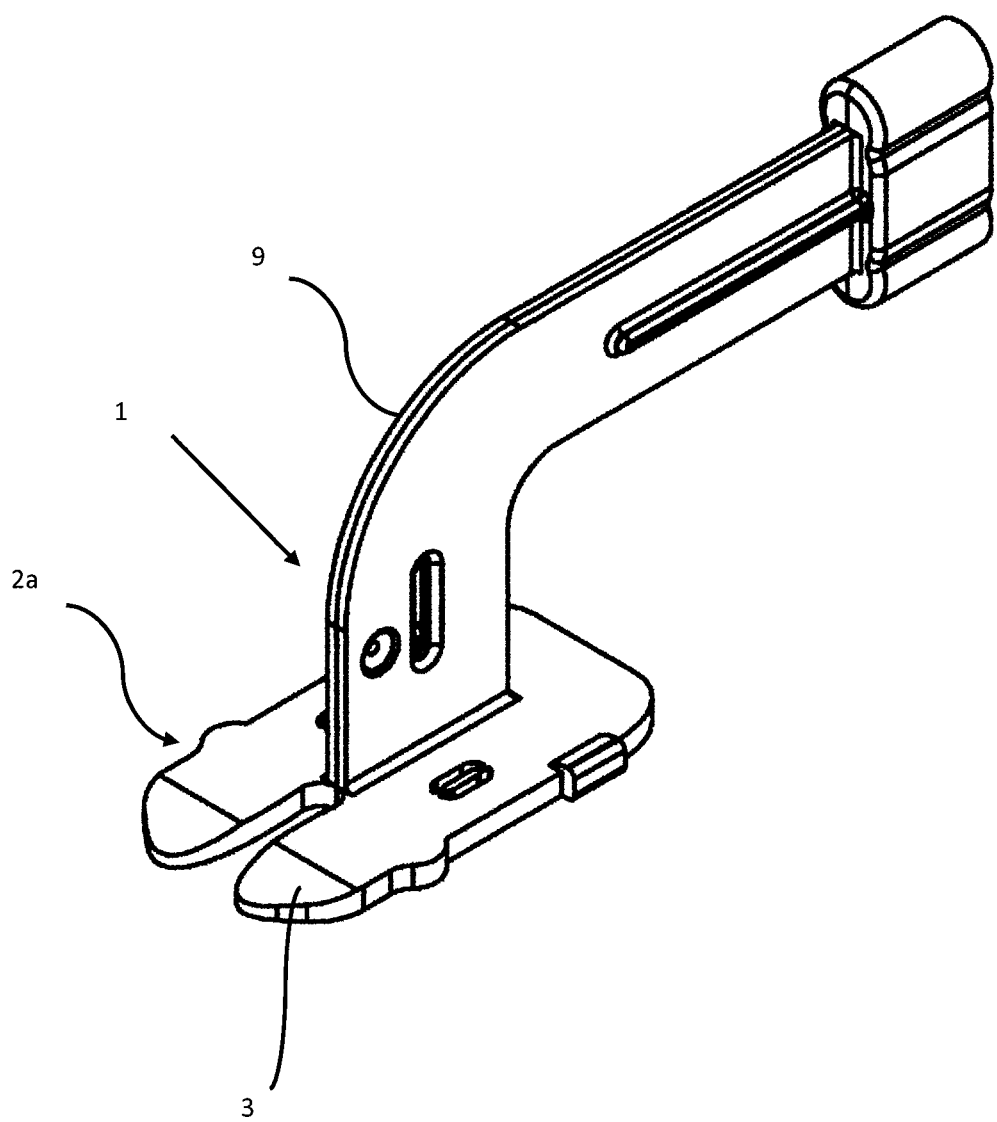
FIG. 20 shows a perspective view of a size 0 bitewing holder.
Figure 27:
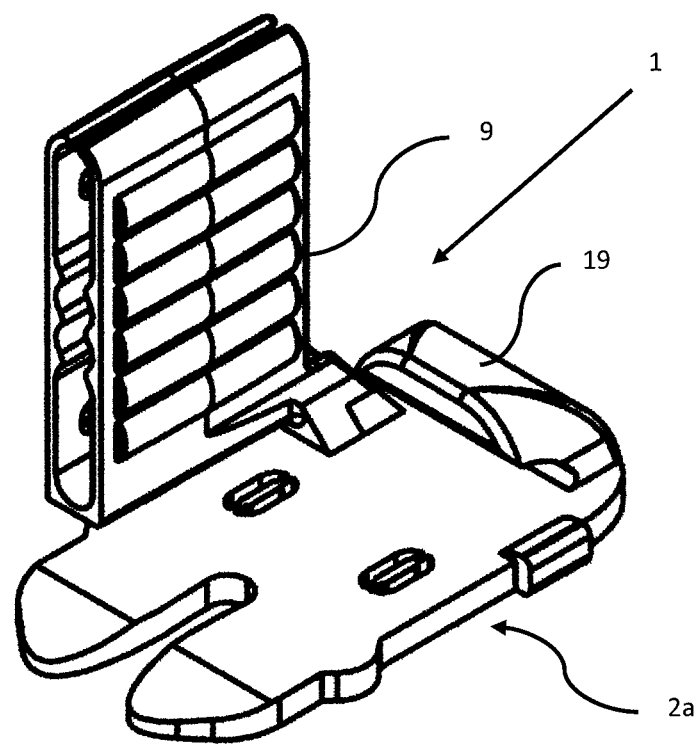
FIG. 27 illustrates a perspective view of a size 0 posterior holder of the present disclosure.

In another embodiment, the holder may comprise different sized biteblocks such as a thick biteblock as shown in FIG. 18, or a thin biteblock as shown in FIG. 19. In further embodiments, the holder may be designed to hold size 0 sensors as shown in FIGS. 17, 20 and 27 for Size 0 anterior, size 0 bitewing and size 0 posterior holders respectively.

Figure 21:
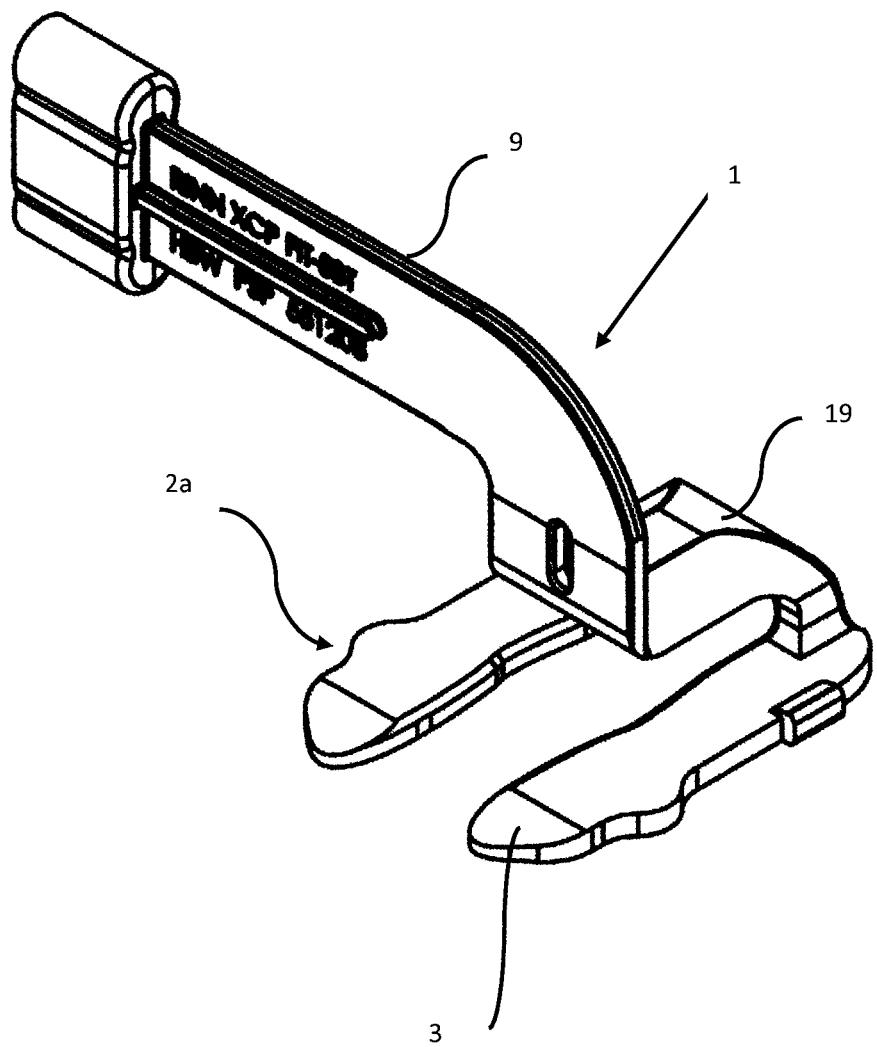
FIG. 21 is a perspective view of a bitewing vertical holder.

FIGS. 21 and 22 show a bitewing vertical 1 and a bitewing horizontal 1 holders respectively. Like some other embodiments, the holders comprise a backing plate 2*a* including two spring arms 3 that extend from a connecting mass 19 at a proximal end of an elongate bite block 9. The bite block 9 may joined to the backing plate 2 at a mid-region so it rests along the occlusal arch of the teeth to be radiographed. Located at a first end 31 of the bite block 9 are slots for a conventional aiming arm (not shown) for connection to an aiming ring (not shown).

It will be appreciated by skilled persons in the art that the elements of the abovementioned embodiments can be extended to other conventional holders such as but not limited to endodontic holders and that many variations of the embodiments are possible without departing from the spirit and scope of the disclosure.

Operation of Preferred Embodiment

The operation of a preferred embodiment, shown in FIG. 1 involves easily sliding a sensor 7 into a sheath of the present disclosure. The backing plate 2 of the holder 1 is then slid in underneath the strap 4 of the sheath 5. The spring arms 3 of the backing plate then pull up on the strap 4 which tighten the sheath 5 to keep the sensor in place. The slot 10 of the bite block 9 is affixed with an aiming arm (not shown) which in turn is affixed with an aiming ring (not shown). The bite block is hereafter positioned in the oral cavity by clenching the buccal surfaces of the maxilliary and mandibular teeth on the block so that the sensor is appropriately positioned, for example, perpendicularly to the interproximal region of the tooth or teeth to be examined. The dental professional can then align the aiming ring and the X-ray unit for image acquisition.

What has been described and illustrated herein is a preferred embodiment of the disclosure along with some of its variations. The terms, descriptions and figures used herein are set forth by way of illustration only and are not meant as limitations. Those skilled in the art will recognize that many variations are possible within the spirit and scope of the disclosure in which all terms are meant in their broadest, reasonable sense unless otherwise indicated. Any headings utilized within the description are for convenience only and have no legal or limiting effect.

INDEX OF ELEMENTS

1: Anterior Holder
1*a*: Bitewing Vertical Holder
1*b*: Bitewing Horizontal Holder
1*c*: Posterior Holder
2: Backing Plate
3: Spring Arm
4: Strap
5: Sheath
6: Phosphor Plate Barrier Envelope
7: Sensor
8: Sensor Cable
9: Bite Block
10: Slot/Aperture
11: Sensor Alignment Tab
12: Channel
13: Arrow
14: Back Film
15: Front Film
16: Top Edge
17: Bend
18: Protective Liner
2*a*: Backing Plate With Two Spring Arms
19: Connecting Mass
20: Tabs
21: Adhesive Applied To Clear Side Of Film
22: Heat Seal Area
23: Back Side Film
24: Clear Side Film
25: Strap
26: Thick Biteblock
27: Notch
28: Envelope
29: Clearance Structure
30: Clearance
31: First End

The invention claimed is:
1. A dental X-ray imaging media holder for holding a sensor for X-ray acquisitions comprising:

a bite block, said bite block having a proximal end, a distal end and a plurality of slots configured to receive an aiming arm for connection to an aiming ring, disposed therein;

a backing plate extending from the proximal end of the bite block constructed to have one or more spring arms, and one or more clearance structures each having a slot of the plurality of slots, wherein the one or more clearance structures are coupled to the backing plate and are configured to provide clearance for movement of a file during dental treatment, wherein the spring arms are separated by a clearance that extends along a fraction or whole of the length of the backing plate, wherein the spring arms are constructed to be compressed inwardly to generate an outward force for holding different sizes of sensors.

2. The dental X-ray imaging media holder of claim 1, further comprising a connecting mass wherein the connecting mass connects the backing plate to the proximal end of the bite block.

3. The dental X-ray imaging media holder of claim 2, wherein the connecting mass has bevel surfaces which are constructed to allow the spring arms to substantially move in a horizontal plane without deflecting upward or downward from said plane.

4. The dental X-ray imaging media holder of claim 1, further comprising tabs constructed to hold a sensor strap in place and/or serve as positioning means for location in an imaging procedure.

5. A dental X-ray sensor sheath comprising:

a protective cover for housing a sensor, the protective cover having a first edge and a second edge;

a strap that is structurally attached, to the protective cover at the first and second edges; and a plurality of "V" shaped notches constructed to be torn along a longitudinal direction to expose the sensor;

wherein, the strap is configured to pull on the protective cover, when said strap is under a pulling force, to tighten said protective cover around the sensor.

6. The dental X-ray sensor sheath according to claim 5 wherein the sensor is a phosphor plate.

7. The dental X-ray sensor sheath according to claim 5 wherein an angle of the V notch is between 45° and 75°.

8. The dental X-ray sensor sheath according to claim 5 wherein an angle of the V notch is 60°.

9. The dental X-ray sensor sheath according to claim 5 wherein the first and second sides are constructed to bulge out such that the envelope is gripped when tearing without pulling on the sensor.

10. The dental X-ray sensor sheath according to claim 5, wherein the protective cover comprises a front side film and a back side film and wherein an adhesive is applied to a portion of the clear side film to enable closing of the sheath.

11. The dental X-ray sensor sheath according to claim 10, wherein the front side film is transparent.

* * * * *